United States Patent [19]
Henry et al.

[11] 4,374,777
[45] Feb. 22, 1983

[54] SYNTHESIS OF HYDROCARBON SOLUBLE VANADIUM CATALYST

[75] Inventors: Ronald A. Henry, China Lake, Calif.; Arnold Adicoff, Burke, Va.

[73] Assignee: The United States of America as represented by the Secretary of the Navy, Washington, D.C.

[21] Appl. No.: 252,712

[22] Filed: Apr. 9, 1981

[51] Int. Cl.³ .............................................. C11C 1/00
[52] U.S. Cl. .............................. 260/414; 252/431 C; 252/431 N
[58] Field of Search .......................... 260/414, 429 R

[56] References Cited

U.S. PATENT DOCUMENTS

| | | | |
|---|---|---|---|
| 1,914,557 | 6/1933 | Craver . | |
| 2,395,307 | 2/1946 | Weber et al. | 260/414 |
| 2,397,767 | 4/1946 | Taylor | 260/414 |
| 2,528,803 | 11/1950 | Unkefer | 260/97.5 |
| 3,162,660 | 12/1964 | Crayton | 260/414 |
| 3,362,972 | 1/1968 | Wallington | 260/414 |
| 3,634,476 | 1/1972 | Rinse | 260/429 |
| 3,689,515 | 9/1972 | Smith, Jr. | 260/429 R |
| 3,723,152 | 3/1973 | Alkaitis et al. | 106/310 |
| 4,162,986 | 7/1979 | Alkaitis et al. | 252/33.2 |
| 4,257,913 | 3/1981 | Fischer | 260/414 |

*Primary Examiner*—John F. Niebling
*Attorney, Agent, or Firm*—Bruce H. Cottrell; W. Thom Skeer; Robert F. Beers

[57] ABSTRACT

A process is disclosed for the preparation of vanadium trineodecanoate to be used as one component of a promoter used in conjunction with a catalyst to cure a polyester resin. Vanadium pentoxide is reacted or reduced in an acidic solution. The resultant mixture is heated and thereupon neodecanoic acid triethyl phosphate, paraformaldehyde and xylene are added. This solution is azeotropically distilled. Vanadium trineodecanoate is recovered in a xylene phase.

1 Claim, No Drawings

SYNTHESIS OF HYDROCARBON SOLUBLE VANADIUM CATALYST

BACKGROUND OF THE INVENTION

1. Field of the Invention

This invention relates to a process for preparing a composition of matter and in particular to a component of a promoter, soluble in hydrocarbons, used to cure a styrenated polyester resin.

2. Description of the Prior Art

The use of promoters as catalysts to increase the curing of polyester resin is well known in the art.

Some promoters do not work well in the presence of water, do not have sufficient shelf-life, or do not increase the rate of cure sufficiently.

SUMMARY OF THE INVENTION

A need arose to lay down a firm surface within a short time in adverse environments sufficient to support light truck or aircraft traffic.

To accomplish this goal, a polyester-glass mat was developed.

Firstly, a glass mat is laid down over the ground surface; next, a polyester resin is mixed with a catalyst and a promoter in the field; further, this mixture is sprayed on the mat and allowed to cure.

The promoter is composed of N,N-dimethyl-p-toluidine and a solution of vanadium (III) trineodecanoate which is soluble in hydrocarbons.

The basic process to obtain the vanadium trineodecanoate is commenced by reacting or reducing vanadium pentoxide with a mixture of formic acid and hydrochloric acid. The resultant mixture is heated for a period of time after which neodecanoic acid, triethyl phosphate, paraformaldehyde, and xylene are added. This solution is azeotropically distilled to remove the aqueous phase while the vanadium (III) salts remain in the xylene.

One object of this invention is a catalyst capable of use in water.

A second object is a catalyst having a sufficiently long shelf-life.

Another object is a catalyst which causes polyester resin to set in less than 15 minutes and fully cure within an hour.

A still further object is a promoter which is soluble in hydrocarbons.

Other objects and novel features of the invention will become apparent from the following description of the invention.

DESCRIPTION OF THE PREFERRED EMBODIMENT

The promoter of the present invention is a mixture of N,N-dimethyl-p-toluidine and vanadium trineodecanoate.

A previous catalyst used has the trademark of Ten-Cem and was manufactured by Mooney Chemicals, Inc. This product was used as a baseline material in the new process of developing vanadium (III) trineodecanoate.

EXAMPLE I

For the preparation of 3% by weight vanadium trineodeconate, the following procedures apply: to a stirred solution of 42 g. of 90% formic acid in 450 ml. of concentrated hydrochloric acid, 54 g. of reagent vanadium pentoxide was added over 5 minutes. The mixture was flushed with nitrogen, and heated to 80° C. and held within 80°–90° C. for 2 hours until no undissolved material existed. Without cooling, 330 g. of prime grade neodecanoic acid, 192 g. of triethyl phosphate (MCB Practical grade), 6 g. of paraformaldehyde and 500 ml. of xylene were added. While maintaining a nitrogen atmosphere, the heterogeneous system was heated rapidly to reflux with very vigorous stirring. The azeotroping aqueous phase was separated in a water trap and removed continuously; depending on the efficiency of the condenser, 410 to 440 ml. of aqueous phase was recovered. The pot temperature during this period was 100°–110° C. and only when most of the water had been removed did the temperature rise slowly to 148°–150° C. About 100 to 120 minutes were required to complete the removal of the aqueous phase. When no more azeotrope distilled, the heating was stopped and the green-colored xylene solution cooled, under a nitrogen atmosphere, to 50° C. and 5 g. of Celite added with stirring. The resultant solution was vacuum-filtered through a Celite mat into a tared flask; the reaction vessel was washed with three 10–20 ml. portions of xylene, each washing being used in turn to wash the Celite mat. The weight of the filtered solution was finally adjusted to 1000 g. with xylene. The catalyst solution should be stored under nitrogen.

EXAMPLE II

In order to lower the cost of development and production, commercial grades were used in the above process. To prepare a 4% vanadium solution, the procedure developed in Example I can be followed with these exceptions. Both the reagent grade vanadium pentoxide and the prime grade neodecanoic acid were replaced by technical grade reactants. Vanadium pentoxide was replaced on an equal weight basis and 363 g. of technical grade neodecanoic acid was used instead of 330 g. Further, the amount of xylene used for azeotroping the excess hydrochloric acid was reduced to 250 ml. The final weight of the filtered solution was adjusted to 750 g. instead of 1000 g. It was found that the catalyst system made from this vanadium neodecanoate solution was as effective as that made from the reagent vanadium pentoxide.

One goal of this invention is to reduce the effects caused by aging. Accelerated aging studies of four different solutions were conducted at 60° C. The ratio of vanadium solution to dimethyl-p-toluidine (DMT) is the same as that used for commercial Ten Cem. Results are given in Table I. In general, a nitrogen atmosphere reduces aging effects and the vanadium solution without the DMT is quite stable even in the presence of air.

The reported gel times in Table I have been obtained using 1.1 phr cumene hydroperoxide with varying amounts of vanadium trineodecanoate solution and DMT. The aging data was carried out with 0.218 phr promoter solution or 0.16 phr of 3% vanadium trineodecanoate solution and 0.12 phr DMT giving a ratio of cumene hydroperoxide to promoter of 4:1.

TABLE I

| Aging of vanadium neodecanoate solutions | | | | |
|---|---|---|---|---|
| Solution | Age (days) | Gel time (min) | Time to max. Temp. (min) | Barcol hardness |
| Promoter soln.[a] | | | | |
| 60° C. under air | 0 | 12.75 | 21 | 44 |
| | 32 | 31 | 51.75 | 48 |

TABLE I-continued

Aging of vanadium neodecanoate solutions

| Solution | Age (days) | Gel time (min) | Time to max. Temp. (min) | Barcol hardness |
|---|---|---|---|---|
| | 78 | 35.5 | 59.5 | 47 |
| Promoter soln.[a] | | | | |
| 60° C. under nitrogen | 0 | 14.1 | 23.4 | 44 |
| | 32 | 23.25 | 39 | 51 |
| | 78 | 21.25 | 34 | 48 |
| Vanadium neodecanoate soln.[b] | 0 | 14.1 | 23.4 | 44 |
| 60° C. under air | 56 | 21.25 | 32.75 | 50 |
| | 78 | 26 | 42.75 | 46 |
| Promoter soln.[a] ambient temperature under air | 0 | 14.1 | 23.4 | 44 |
| | 32 | 29.25 | 48.5 | 52 |
| | 78 | 28.5 | 46.5 | 48 |

[a]Vanadium neodecanoate to DMT ratio = 1.34 to 1.0.
[b]DMT (not aged at 60° C.) added for gel time determination.

The effect of vanadium trineodecanoate in the promoter solution was determined. The different percentage concentrations were obtained by adding or removing xylene from the 3% solution. The ratio of vanadium salt to DMT was 1:1. The resulting gel times of the three different concentrations is illustrated in Table II.

TABLE II

Effect of Vanadium Trineodecanoate (VTN) Concentration on Reaction Times

| Initial VTN Conc. (%) | Amt. VTN Soln. added (phr) | Amt. DMT added (phr) | Gel Time (min) | Time to Max. Temp. (min) | Barcol Hardness |
|---|---|---|---|---|---|
| 2 | 0.14 | 0.14 | 53.25 | 94.25 | 51 |
| | .185 | .185 | 25 | 40 | 47 |
| | .275 | .275 | 8.25 | 14.25 | 48 |
| 3 | 0.14 | 0.14 | 22.75 | 36 | 52 |
| | .185 | .185 | 9.75 | 15.5 | 52 |
| | .275 | .275 | 4.25 | 7.5 | 54 |
| 4 | 0.14 | 0.14 | 10.5 | 17.25 | 51 |
| | .185 | .185 | 5.75 | 10 | 55 |
| | .275 | .275 | 2.5 | 5 | 54 |

In order to obtain more convenient gel times, a 4% vanadium salt solution was prepared. This solution was then used with DMT (ratio 1:1) for preparing a promoter solution for an accelerated aging studies at 60° C. Results are shown in Table III.

TABLE III

Comparison of Various 4% Vanadium Trineodecanoate (VTN) Solutions

| VTN Soln. | Amt. VTN Soln. added (phr) | Amt. DMT added (phr) | Gel Time (min) | Time to Max. Temp. (min) | Barcol Hardness |
|---|---|---|---|---|---|
| 954-30[1] | 0.14 | 0.14 | 10.5 | 17.25 | 51 |
| | 0.185 | 0.185 | 5.75 | 10 | 55 |
| 956-22[2] | 0.14 | 0.14 | 12.5 | 20 | 48 |
| | 0.185 | 0.185 | 6 | 10.5 | 47 |
| 956-122[3] | 0.14 | 0.14 | 12 | 19.25 | 45 |
| | 0.185 | 0.185 | 7 | 11.5 | 48 |

[1]Originally contained 3% VTN; xylene evaporated off to give 4% VTN; made with reagent grade V$_2$O$_5$ and prime grade neodecanoic acid.
[2]Made with technical grade V$_2$O$_5$ and prime grade neodecanoic acid.
[3]Made with technical grade V$_2$O$_5$ and technical grade neodecanoic acid.

Flexural strengths of the composite laminates were measured according to ASTM D790-71 using a 3-point bending apparatus in an Instron testing machine.

Several 9×12 inch 2-ply laminates using Fabmat C-4020 were made. Ten Cem was the promoter for two of the laminates in one of which the glass mats contained approximately 71% water.

Two laminates were also made using the vanadium neodecanoate solution. The fiberglass mats in one of these contained about 68% water. These laminates were cut up into various configurations for testing. Strips for the measurements are approximately 13 mm×127 mm×6 mm and the supports are 86 mm apart. Results are illustrated in Table IV.

TABLE IV

Flexural Strengths of Polyester-Glass Mat Laminates

| Laminate | VTN Soln. used[1] | Resin Content % | Initial Water Content in Glass Mat, % | Ave. Flexural Strength[2] GPa | psi |
|---|---|---|---|---|---|
| 21 | Ten Cem | 55.6 | — | 0.271 | 39,300 |
| 30 | Ten Cem | 57.6 | 71.0 | 0.162 | 23,500 |
| 28 | 954-121[3] | 55.6 | — | 0.368 | 53,400 |
| 29 | 954-121 | 55.9 | 67.8 | 0.243 | 35,300 |

[1]Promoter solution had VTN to DMT ratio of 1.34:1 by wt.
[2]Average obtained from 5 or 6 samples.
[3]VTN concentration is 3%.

What is claimed is:

1. A process for the production of vanadium trineodecanoate to be used with a promoter as a catalyst comprising the steps of:
   reducing vanadium pentoxide in an acidic solution of formic and hydrochloric acids to form a vanadium (III) solution;
   heating said vanadium (III) solution under nitrogen for a period of time at 80°–90° C.;
   adding neodecanoic acid, triethyl phosphate, paraformaldehyde and xylene to said heated vanadium (III) solution to form a heterogeneous solution;
   heating said heterogeneous solution rapidly to reflux with stirring;
   azeotropically distilling said heterogeneous solution under nitrogen to remove the aqueous phase; and
   recovering said vanadium trineodecanoate in a xylene solution.

* * * * *